United States Patent [19]

Zimmerman et al.

[11] 4,236,009

[45] Nov. 25, 1980

[54] METHOD OF PREPARING 4A-ARYLHEXAHYDRO-1H-2-PYRINDINES AND 4A-ARYLOCTAHYDROISOQUINOLINES

[75] Inventors: Dennis M. Zimmerman, Mooresville; Roger L. Robey, Greenwood, both of Ind.

[73] Assignee: Eli Lilly and Company, Indianapolis, Ind.

[21] Appl. No.: 50,940

[22] Filed: Jun. 21, 1979

[51] Int. Cl.$^3$ .................. C07D 217/04; C07D 221/04
[52] U.S. Cl. ..................................... 546/112; 424/258; 546/144; 546/302; 546/303
[58] Field of Search ................. 546/112, 144, 302, 303

[56] References Cited

U.S. PATENT DOCUMENTS

| | | | |
|---|---|---|---|
| 4,001,247 | 1/1977 | Zimmerman et al. | 424/258 X |
| 4,001,248 | 1/1977 | Zimmerman et al. | 424/258 X |
| 4,029,796 | 6/1977 | Zimmerman et al. | 424/258 OR |
| 4,100,166 | 6/1978 | Zimmerman et al. | 424/258 X |

FOREIGN PATENT DOCUMENTS

| | | | |
|---|---|---|---|
| 802557 | 11/1973 | Belgium | 546/144 |
| 860314 | 4/1978 | Belgium | 546/144 |

OTHER PUBLICATIONS

Zimmerman et al., Chem. Abstracts, vol. 84, abst. 90,020t and 90021u, (1976).
Zimmerman et al., Chem. Abstracts, vol. 84, abst. 121,667 r, (1976).
Zimmerman et al., Chem. Abstracts, vol. 84, abst. 150,562 z, (1976).
Weller et al., Chem. Abst. vol. 86,189670 h, (1977).

*Primary Examiner*—John D. Randolph
*Attorney, Agent, or Firm*—James L. Rowe; Arthur R. Whale

[57] ABSTRACT

4a-Arylhexahydro-1H-2-pyrindines and 4a-aryloctahydroquinolines analgesic agonists and antagonists are prepared doubly alkylating a 4-aryltetrahydropyridine with an $\alpha,\omega$-dihaloalkane.

3 Claims, No Drawings

METHOD OF PREPARING 4A-ARYLHEXAHYDRO-1H-2-PYRINDINES AND 4A-ARYLOCTAHYDROISOQUINOLINES

BACKGROUND OF THE INVENTION

4a-Phenyl(or substituted phenyl)octahydro-1H-2-pyrindines are disclosed in Belgian Pat. 860,314 as being useful analgesic agents having mixed agonist-antagonist properties. These compounds can be represented by the following formula:

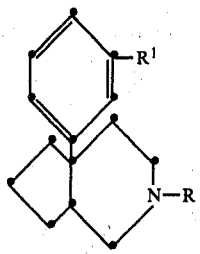

wherein R is H, ($C_1$-$C_8$)alkyl etc. and $R^1$ is H, alkoxy, OH or alkanoyloxy. 4a-Phenyloctahydro-1H-2-pyrindines of the above formula can be prepared by the following reaction sequence: A 2-arylcyclohexanone is alkylated at the 2-position by reaction with an α-halo acetate in the presence of base. The product of this reaction, a 2-aryl-2-alkoxycarbonylmethylcyclohexanone, is next formylated at the 6-position by reaction with ethyl formate in the presence of metallic sodium. The 2-aryl-2-alkoxycarbonylmethyl-6-formylcyclohexanone thus prepared is next reacted with p-tosylazide to provide a 2-aryl-2-alkoxycarbonylmethyl-6-diazocyclohexanone. Photolysis of the diazo compound results in a ring contraction, the product of the reaction being a 2-aryl-2-alkoxycarbonylmethyl-1-methoxycarbonylcyclopentane. Hydroxylsis of this compound provides the corresponding diacid, 2-aryl-2-hydroxycarbonylmethyl-1-hydroxycarbonylcyclopentane. Cyclization of this diacid derivative with an acid halide such as acetyl chloride provides the corresponding anhydride, a 4a-aryl-tetrahydro-2,6-dioxocyclopenta[c]pyran. Reaction of this dioxopyran with ammonia or a primary amine ($R^2$-$NH_2$) yields a cyclic imide; to wit, a 1,3-dioxo-4a-aryl-2,3,4,4a,5,6,7,7a-octahydro-1H-2-pyrindine. The dioxopyrindine can then be reduced as with lithium aluminum hydride to yield a 4a-aryl-octahydro-1H-2-pyrindine of formula I. If the product of the synthesis produces a secondary amine, (R is H), other N-derivatives can be prepared as follows:

The secondary amine can be alkylated as with methyl iodide or phenethylbromide in a standard alkylation procedure to yield an N-alkyl (or substituted alkyl) derivative or may be acylated as by cyclopropylcarboxyl chloride to yield a 2-acyl derivative which can in turn be reduced as with lithium aluminum hydride to an alkyl yielding, in this instance, an N-cyclopropylmethyl derivative.

4a-Aryl-trans-dl-decahydroisoquinolines of Formula II below are described in Belgian Pat. No. 802,557 and in a series of U.S. Pat. Nos. 4,001,247; 4,001,248; 4,029,796 (each of which describes the preparation of both cis and trans- compounds); and U.S. Pat. No. 4,100,166, which describes the preparation of certain cis- derivatives corresponding to the trans- derivatives of the Belgian patent.

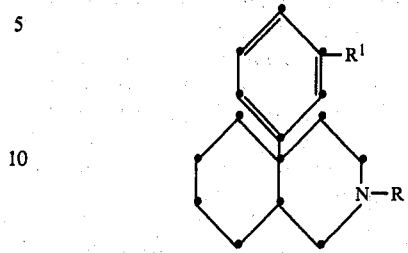

wherein R and R1 have substantially the same meaning as hereinabove.

U.S. Pat. No. 4,001,247 describes several methods of preparing decahydroisoquinolines. The first procedure begins with the reaction of a 2-arylcyclohexanone with acrylonitrile to yield a 2-phenyl-2-(β-ethyl)cyclohexanone. The nitrile group is hydrolyzed to a carboxylic acid function, the corresponding azide prepared and the azide converted to the isocyanate. Treatment of the isocyanate with acid yields a 3a-aryl-2,3,3a,4,-5,6,7-heptahydroindole. Next the heptahydroindole is acylated to yield a N-methyltetrafluoroborate quaternary salt. The reaction of this salt with diazomethane produces a salt of a 1-azonia-1-methyl-4-aryltricyclodecane, rearrangement of which by treatment with heat and alkali produces a 2-methyl-4a-aryl-2,3,4,4a,5,6,7,8-octahydroisoquinoline. The double bond in this compound can be hydrogenated to yield either a cis- or trans-decahydroisoquinoline. In addition, the methyl group can be removed to yield a secondary amine which can be realkylated to yield a veriety of N-substituted-4a-aryldecahydroisoquinolines, as set forth above for the corresponding 4a-aryloctahydro-1H-2-pyrindines.

A second reaction sequence disclosed in U.S. Pat. No. 4,100,166 involves the alkylation of a 2-arylcycloheptanone with bromoacetic ester to yield a 2-aryl-2-(ethoxycarbonylmethyl)cycloheptanone. This compound is formylated to yield a 7-formyl derivative, treatment of which with p-tosylazide yields the corresponding 7-azido compound. Treatment of this azido compound with methanol results in a molecular rearrangement, the ultimate product of which is a 2-aryl-2-ethoxycarbonylmethylcyclohexanecarboxylic acid ester, isolated as a mixture of cis- and trans- derivative. Saponification of the diester followed by treatment with an acid chloride yields the corresponding cyclic anhydride named as a cis(or trans)-3,4,4a,5,6,7,8,8a-octahydro-1,3-dioxo-1H-2-benzopyran. This intermediate is similar to those employed for the preparation of the pyrindines as described in Belgian Pat. No. 860,314 and the same series of reactions; i.e., reaction with a primary amine followed by reduction of the resulting imide, yields directly the cis (or trans)-4a-aryl-N-substituted-decahydroisoquinoline.

Brittelli and Ripka in Belgian Pat. No. 802,557 disclose a still different method of preparing the 4a-aryldecahydroisoquinolines. This procedure begins with a 2-cyano-3-aryl-3-ethoxycarbonylmethylcyclohexene which can be cyclized in the presence of acid to yield a 4a-aryl-1,3-diox-1,2,3,4,4a,5,6,7-octahydroisoquinoline. This imide is customarily alkylated to yield an N-substituted product prior to reduction of the 8,8a-double bond (which produces a trans-derivative) and finally by removal of the dioxo groups by reduction with lithium aluminum hydride. Reduction of the 8,8a-double bond can also take place prior to reduction of the imide and the trans-dioxo-decahydroisoquinoline can be epimerized to the corresponding cis derivative.

Each of the above synthetic procedures involves a large number of steps and many of these steps afford the possibility of by-product formation. Furthermore, one of the procedures for preparing the above decahydroisoquinolines involves the use of the toxic and explosive substance, diazomethane. In addition, the procedures outlined above for the preparation of the decahydroisoquinolines have been found to be inoperative for the preparation of octahydropyrindines.

It is an object of this invention to provide a short and simplified process for the preparation of either octahydropyrindines or decahydroisoquinolines carrying an aryl substituent at the bridge-head carbon, which synthesis can provide the desired products in either cis- or trans configuration.

SUMMARY OF THE INVENTION

In fulfillment of the above and other objects, this invention provides a procedure for the preparation of 4a-aryloctahydropyrindines and 4a-aryldecahydroisoquinolines containing the following reaction steps:

(1) reaction of phenyllithium (permissibly substituted at a meta-position) with a 1-alkyl or 1-benzyl-4-piperidone to yield the corresponding 1-alkyl (or benzyl) 4-phenyl-4-hydroxypiperidine.

(2) dehydration to yield a 1-alkyl (or benzyl)-4-(permissibly-substituted) aryl-1,2,3,6-tetrahydropyridine.

(3) reaction of the tetrahydropyridine thus formed with n-butyllithium to form a carbanion and reacting said carbanion with a propylene or butylene dihalide of the formula

wherein each Y is H, CH$_3$ or C$_2$H$_5$, n is 3 or 4 and X and X' are chlorine, bromine or iodine to yield a 1-alkyl (or benzyl)-4-(permissibly-substituted)aryl-4-(ω-haloalkyl)-1,4,5,6-tetrahydropyridine.

(4) internal cyclization of the alkylated tetrahydropyridine using, for example, sodium iodide in dilute acetonitrile solution to provide the corresponding 2-alkyl(or benzyl)-4a-(permissibly-m-substituted) aryl-3,4,4a,5,6,7-hexahydro-2-pyrindine or 2,3,4,4a,5,6,7,8-octahydroisoquinoline of the formula:

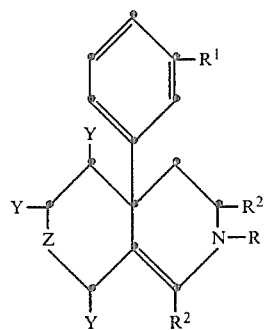

wherein R is (C$_1$-C$_3$)alkyl, (C$_3$-C$_4$)cycloalkylmethyl, benzyl or phenethyl, R$^1$ is H or (C$_1$-C$_3$)alkyloxy, Z is

or a direct bond and each R$^2$ and Y is independently H or (C$_1$-C$_2$)alkyl.

(5) followed by hydrogenation to yield either a cis- or trans-octahydropyrindine or decahydroisoquinoline of the formula:

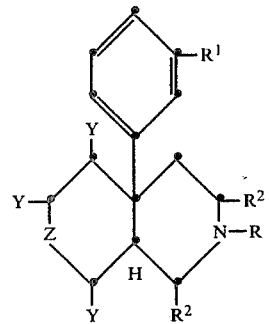

wherein R, R$^1$, R$^2$, Y and Z have the same meaning as hereinbefore.

The term (C$_1$-C$_3$)alkyl includes methyl, ethyl and propyl and the term (C$_3$-C$_4$)cycloalkyl, cyclopropyl and cyclobutyl.

This invention is more graphically illustrated by the following Reaction Scheme.

Reaction Scheme I

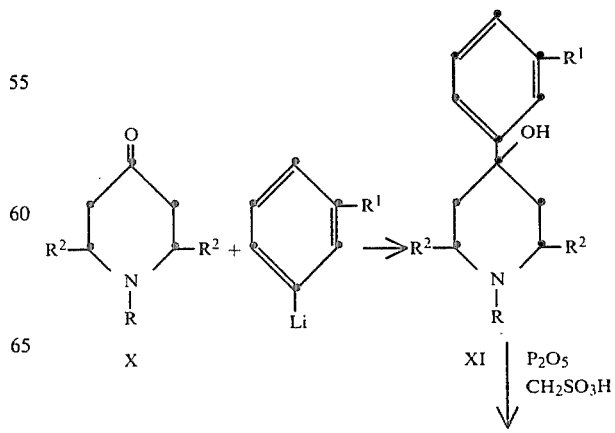

-continued
Reaction Scheme I

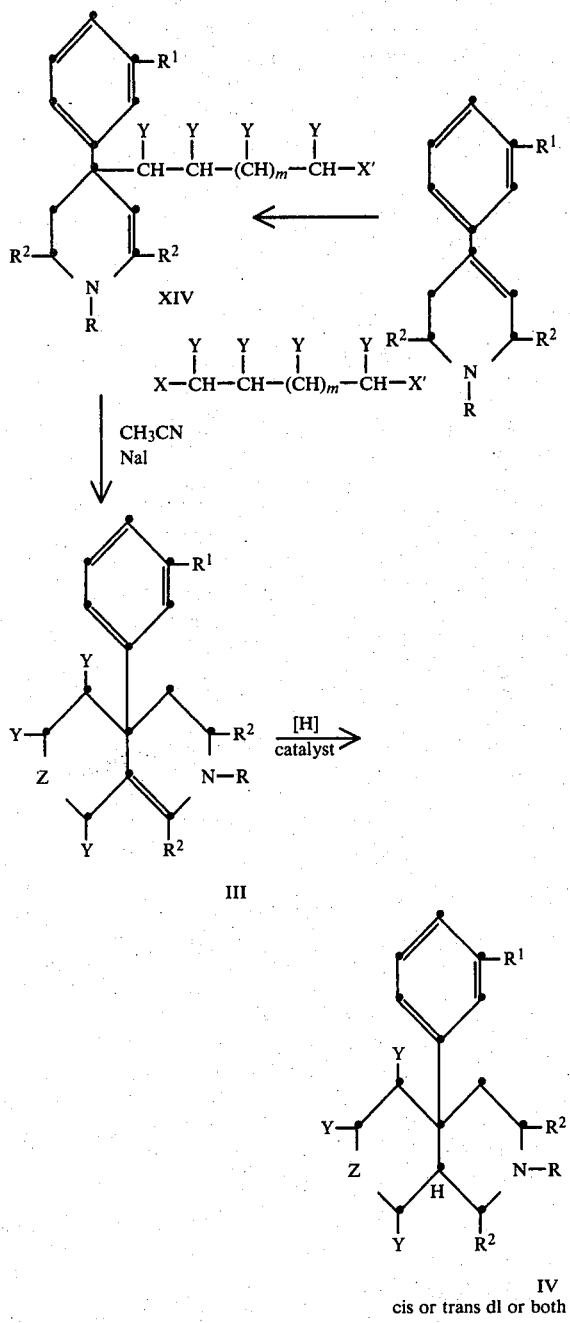

III

IV
cis or trans dl or both

In the above Reaction Scheme, R, $R^1$, $R^2$, X, X', Y and retain their previous significance and m is 0 or 1.

According to Reaction Scheme I, an N-alkyl(or benzyl) 4-piperidone, permissibly substituted at carbons 2 or 6 of the piperidone ring with one or more methyl or ethyl groups, is reacted with phenyllithium or m-methoxyphenyllithium to yield an N-alkyl(or benzyl) 4-phenyl-4-hydroxypiperidone, permissibly substituted with ethyl or methyl at carbons 2 and 6 (II). Phenyllithium or 3-methoxyphenyllithium is prepared by reaction of the corresponding bromobenzene or 3-methoxybromobenzene with n-butyl lithium in an inert, perferably a hydrocarbon, solvent. In this reaction, the lithium and bromine atoms interchange to yield n-butylbromide as a byproduct plus the desired phenyllithium or 3-methoxyphenyllithium. A solution of the piperidone in an inert hydrocarbon solvent or ethereal solvent is added thereto and the reaction carried out simply by stirring at ambient temperature.

The 4-hydroxypiperidine thus formed is next dehydrated to yield the corresponding 1,2,5,6,-tetrahydropyridine(XII). This dehydration can be accomplished by treating the tertiary hydroxy compound with a dehydrating agent such as phosphorus pentoxide in a solvent such as methanesulfonic acid. Alternatively, the dehydration can be accomplished by reacting the tertiary hydroxyl-containing piperidine with a catalytic quantity of a strong acid such as p-toluenesulfonic acid, also in an inert solvent.

Next, the N-alkyl(or benzyl) 4-phenyl(or m-methoxyphenyl) 1,2,5,6-tetrahydropyridine is alkylated with a 1,3-dihalopropane or a 1,4-dihalobutane representated by the structure

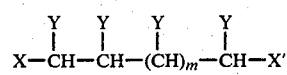

in which X and X' are the same or different halogens of the group consisting of chlorine, bromine and iodine, each Y is independently hydrogen, methyl or ethyl and m is 0 or 1. The product of this reaction is an N-alkyl(or benzyl)-4-phenyl(or m-methoxyphenyl)-4-haloalkyl-1,4,5,6-tetrahydropyridine permissibly substituted with one or more methyl or ethyl groups at C-2, or C-6 (XIV). In the alkylation reaction, the most reactive halogen of the dihaloalkane will react preferentially at the 4 position of the pyrindine ring. If the alkylating agent (XIII) is unsubstituted; i.e., all Y's are hydrogen, the alkyl group may have the same halogen atoms at each end of the chain. For example, in such a case, the alkylating agent could be a 1,3-dibromopropane or a 1,4-dichlorobutane. The same situation would be present if any symmetrical alkylating agents is used as for example 1,3-dibromo-2-methylpropane or 1,4-dibromo-2,3-dimethylbutane as well as 1,3-dibromopropane etc. In general, however, I prefer to employ alkylating agents in which X and X' do represent different halogen atoms. We have found that the use of halogens of different reactivity tends to minimize dimer formation even in a symmetrical alkane. In other words, use, for example, of a 1,3-diiodopropane might result in product of a significant amount of an undesired by-product in which two pyridines are linked through a propane group at C-4. By employing an alkylating agent in which the halogens atoms are different, our preferred mode, the reaction conditions which will suffice to cause a reaction to the place between the iodo group in a 1-iodo-3-bromopropane, for example, to cause it to react at C-4 of the pyridine would not be sufficiently stringent to cause any large quantity of the resulting omega-bromopropyl derivative to react with a second molecule of the pyridine to yield a "dimeric" by-product. It is, of course, true that a dimerization reaction can be minimized by utilizing low reaction temperature or dilute solutions or both and by adding the tetrahydropyridine compound to a solution of the alkylating agent—the dihaloalkane. During of the alkylation at C-4, the 3, 4 double bond migrates to the 2, 3-position to yield an enamine. We customarily carry out the alkylation by reacting the tetrahydropyridine (XII) with n-butyl lithium, thus forming a carbanion at C-2. This carbanion is part of an allylic system and can quickly rearrange to yield a carbanion at C-4, the C-4 carbanion being energetically more stable. It is probably during the formation of the carbanion that the double bond migration referred to above takes place.

Finally, the alkylated enamine (XIV) is internally cyclized in the presence of sodium iodide in a dilute acetonitrile solution to yield a hexahydropyrindine or octahydroisoquinoline, depending upon the value of the "Z".

Internal alkylation by the C-4 ω-haloalkyl group takes place on the adjacent carbon at C-3, leaving the double bond in the same relative position in the pyrindine and isoquinoline as it was in the tetrahydropyridine starting material.

This invention is further illustrated by the following specific examples:

EXAMPLE 1

1-Methyl-4-hydroxy-4-(3-methoxyphenyl)piperidine

A solution of 159 ml. of n-butyl lithium in 100 ml. of hexane containing 47.7 g. of 3-methoxybromobenzene was stirred at −25° C. for twenty minutes and then was warmed to room temperature at which temperature it was stirred for one hour, thus providing 3-methoxyphenyllithium. The reaction mixture was chilled to 10° C. and stirred while a solution of 50 g. of 1-methyl-4-piperidone in 100 ml. of diethyl ether was added in dropwise fashion over a thirty minute period. Following the completion of the addition, the reaction mixture was stirred for two additional hours, and was then mixed with 50 ml. of saturated aqueous sodium chloride solution. The aqueous solution was extracted several times with diethyl ether, and the ethereal extracts were combined and concentrated to dryness to provide 38 g. of 1-methyl-4-hydroxy-4-(3-methoxyphenyl)piperidine formed in the above reaction.

EXAMPLE 2

1-Methyl-4-(3-methoxyphenyl)-1,2,3,6-tetrahydropyridine

To a stirred solution of 200 ml. of 50 g. of phosphorous pentoxide in methanesulfonic acid was added portionwise over four minutes 59 g. of 1-methyl-4-hydroxy-4-(3-hydroxyphenyl)piperidine. The reaction was exothermic, the temperature rising to 70° C. After complete addition of the piperidine derivative, the reaction mixture was poured onto 200 g. of ice, and the resulting aqueous mixture made alkaline by the addition of ammonium hydroxide. The alkaline mixture was extracted several times with diethyl ether, and the ethereal extracts were combined, washed with water, dried, and the solvent removed by evaporation under reduced pressure to provide 44.7 g. of an oil. The oil was distilled to provide 1-methyl-4-(3-methoxyphenyl)-1,2,5,6-tetrahydropyridine; B.P.=123°–138° C. at 0.1 torr.

Analysis Calc. for C₁₃H₁₇NO: Theory: C, 76.81; H, 8.43; N, 6.89: Found: C, 76.52; H, 8.15; N, 6.67.

EXAMPLE 3

4a-Phenyl-2-methyl-3,4,4a,5,6,7-hexahydro-2-pyrindine

To a stirred cold (−5° to −10° C.) solution of 25 g. of 1-methyl-4-phenyl-1,2,5,6-tetrahydropyridine in 450 ml. of tetrahydrofuran was added dropwise over thirty minutes 90 ml. of 1.6 molar n-butyllithium in hexane. Following completion of the addition, the solution was stirred for ten minutes at −10° C. and then cooled to −30° C. The cold solution next was added in dropwise fashion over a twenty minute period to a stirred solution of 73.3 g. of 3-chloropropylbromide in 300 ml. of diethyl ether chilled to −50° C. Following completion of the addition, the reaction mixture was warmed to −20° C. and diluted with 500 ml. of saturated aqueous sodium chloride chilled to 0° C. The organic layer was separated, washed with water, and the desired product was extracted therefrom with 1200 ml. of 1 N hydrochloric acid. The aqueous acidic layer was washed with diethyl ether and the ether extracted discarded. The acidic aqueous solution was then made alkaline by the dropwise addition of concentrated aqueous sodium hydroxide. The resulting alkaline solution was extracted several times with diethyl ether, and the ethereal extracts were combined, washed with water and dried. Evaporation of the solvent at 10° C. afforded an oil which was dissolved in 2500 ml. of acetonitrile containing 52.5 g. of sodium iodide. The reaction mixture was heated at reflux temperature with stirring for twenty-four hours, after which time the solvent was removed by evaporation under reduced pressure. The crude product thus formed was dissolved in a mixture of 800 ml. of 1 N sodium hydroxide and 1000 ml. of diethyl ether, and the mixture was stirred vigorously for forty-five minutes. The ethereal layer then was separated, washed with saturated aqueous sodium chloride and dried. Removal of the solvent by evaporation under reduced pressure afforded the product as an oil, which, upon distillation, provided 21.5 g. of 4a-phenyl-2-methyl-3,4,4a,5,6,7-hexahydro-2-pyrindine; B.P.=110°–112° C. at 0.075 torr.

Analysis Calc. for C₁₅H₁₉N: Theory: C, 84.46; H, 8.89; N, 6.57: Found: C, 84.74; H, 8.72; N, 6.28.

EXAMPLE 4

Following the procedure of Example 3, 1-methyl-4-(3-methoxyphenyl)-1,2,3,6-tetrahydropyridine was reacted with 3-chloropropylbromide and the resulting 4-(ω-haloalkyl) derivative cyclized with sodium iodide to afford 4a-(3-methoxyphenyl)-2-methyl-3,4,4a,5,6,7-hexahydro-2-pyrindine; B.P.=132°–134° C. at 0.1 torr.

Analysis Calc. for C₁₆H₂₂NO: Theory: C, 78.97; H, 8.70; N, 5.76: Found: C, 76.58; H, 8.28; N, 5.36.

m/e: theory 243; found 243.

EXAMPLE 5 trans-4a-Phenyl-2-methyl-2,3,4,4a,5,6,7,7a-octahydro-1H-2-pyrindine

A solution of 5.0 g. of 4a-phenyl-1-methyl-3,4,4a,5,6,7-hexahydro-2-pyrindine in 50 ml. of ethanol containing 500 mg of platinum oxide was stirred at room temperature for four hours under a hydrogen atmosphere of 60 p.s.i. The hydrogenation mixture was filtered to remove the catalyst and the filtrate concentrated by evaporation to provide an oil which was shown by NMR and high pressure liquid chromatography to consist of about forty percent cis-4a-phenyl-1-methyl-2,3,4,4a,5,6,7,7a-octahydro-1H-2-pyrindine and about sixty percent of the corresponding trans isomer. The mixture was dissolved in 50 ml. of diethyl ether and the resulting solution made acidic by the addition of a saturated solution of hydrogen bromide dissolved in diethyl ether. Concentration of the ethereal solution effected crystallization of a hydrobromide salt. The salt was filtered and the precipitate recrystallized from 30 ml. of isopropanol and 70 ml. of diisopropyl ether to afford 2.6 g. of cis-4a-phenyl-2-methyl-2,3,4,4a,5,6,7,7a-actahydro-1H-2-pyrindinium bromide.

The filtrate was evaporated to dryness and the resulting residue dissolved in water. The aqueous solution was made alkaline by the addition of 1 N aqueous sodium hydroxide, and the aqueous alkaline solution was extracted with diethyl ether. The ethereal extracts were combined, washed with water and dried. Removal of the solvent by evaporation under reduced pressure afforded 2.57 g. of trans-4a-phenyl-2-methyl-2,3,4,4a,5,6,7,7a-octahydro-1H-2-pyrindine.

The trans-pyrindine derivative was dissolved in 120 ml. of ethanol and reacted with 2.76 g. of picric acid to provide 2.7 g. of trans-4a-phenyl-2-methyl-2,3,4,4a,5,6,7,7a-octahydro-1H-2-pyrindinium picrate; M.P.=167°-16° C.

Analysis Calc. for $C_{21}H_{24}N_4O_7$: Theory: C, 56.75; H, 5.44; N, 12.61: Found: C, 56.99; H, 5.65; N, 12.46.

The corresponding maleate salt was prepared in similar fashion. trans-4a-Phenyl-2-methyl-2,3,4,4a,5,6,7,7a-octahydro-1H-2-pyrindinium maleate. Melted at 113°-114° C.

Analysis Calc. for $C_{19}H_{25}NO_4$: Theory: C, 68.86; H, 7.60; N, 4.23: Found: C, 68.66; H, 7.83; N, 3.98.

EXAMPLE 6

Following the procedure set forth in Example 5, 4a-(3-methoxyphenyl)-2-methyl-3,4,4a,5,6,7-hexahydro-2-pyrindine was hydrogenated over platinum oxide to provide a 60:40 mixture of trans-4-a-(3-methoxyphenyl)-2-methyl-2,3,4,4a,5,6,7,7a-octahydro-1H-2-pyrindine and the corresponding cisosomer. The trans isomer was crystallized as the picrate salt. The cis isomer was isolated as the free base, namely cis-4a-(3-methoxyphenyl)-2-methyl-2,3,4,4a,5,6,7,7a-octahydro-1H-2-pyrindine; M.P.=40°-43° C.

Analysis Calc. for $C_{16}H_{23}NO$: Theory: C, 78.32; H, 9.45; N, 5.71: Found: C, 78.26; H, 9.31; N, 5.61.

EXAMPLE 7

1-Methyl-4a-phenyl-2,3,4,4a,5,6,7,8-octahydroisoquinoline

Following the procedure of Example 3, 25 g. of 1-methyl-4-phenyl-1,2,3,6-tetrahydropyridine was dissolved in 450 ml. of THF. The solution was cooled and 90 ml. of a 1.6 molar n-butyllithium solution in hexane added thereto in dropwise fashion. Next, 8.23 g. of 1-bromo-4-chlorobutane were added as a chilled solution. As the addition was carried out, the temperatures rose to about 20° C. 1-Methyl-4-phenyl-4-(ω-chlorobutyl-1,4,5,6-tetrahydropyridine, the product of the reaction, was isolated by the procedure of Example 3 and was dissolved, without further purification, in 2500 ml. of acetonitrile containing 52.5 g. of sodium iodide. The reaction mixture was heated to refluxing temperature for about 1 day and the product of the reaction, 1-methyl-4a-phenyl-2,3,4,4a,5,6,7,8-octahydroisoquinoline, was isolated by the procedure of Example 3 and purified by distillation. The compound distilled in the range 115°-120° C. at 0.05 torr.; yield=17.6 g.

Analysis Calc. for C, 84.53; H, 9.31; N, 6.16: Found: C, 84.26; H, 9.12; N, 6.23.

Following the above procedure but substituting 1-methyl-4-(3-methoxyphenyl)-1,2,5,6-tetrahydropyridine for 1-methyl-4-phenyl-1,2,5,6-tetrahydropyridine, there was prepared 1-methyl-4a-(3-methoxyphenyl)-2,3,4,4a,5,6,7,8-octahydroisoquinoline. The compound distilled in the range 144°-6° C. at 0.1 torr.; yield 19.3 g.

Both the above octahydroisoquinolines can be hydrogenated to yield the corresponding cis and trans decahydroisoquinolines.

The novel process of this invention has been illustrated with respect to compounds in which R is methyl, but is readily apparent to those skilled in the art that R could be any group not susceptible to hydrogenation including ethyl, cyclo butylmethyl, cyclopropylmethyl, benzyl and the like.

Compounds prepareable by the processes of this invention are analgetics possessing also to a greater or lesser degree both analgesic agonist and antagonist properties. In addition, compounds in which R is methyl or benzyl can be transformed by standard procedures into compounds in which R is ethyl, n-propyl, cyclopropylmethyl and the like as well as groups not coming within the scope of R in the above formula, including groups which are susceptible to hydrogenation such as allyl, 2-methylbutenyl and the like.

In addition, the above procedure has been illustrated with respect to compounds of which $R^1$ is an alkoxy group. The final octahydropyridine and decahydroisoquinoles in which $R^1$ is alkoxy are also useful intermediates in that they can be demethylated to yield the corresponding compounds in which $R^1$ is hydroxy. These 4a-meta-hydroxyphenyl derivatives are in general more powerful analgesic-antagonist or agonist compounds in the octahydropyridine and decahydroisoquinoline series than the corresponding methoxy derivatives.

We claim:

1. The process which comprises essentially the steps of (a) preparing a lithium derivative of the formula

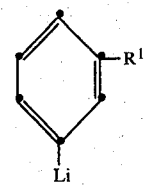

wherein $R^1$ is H or $(C_1-C_3)$alkyloxy and reacting it with a 4-phenyl piperidine of the formula

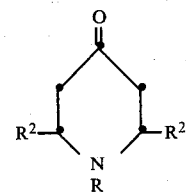

wherein R is $(C_1-C_3)$alkyl, $(C_3-C_4)$cycloalkylmethyl, benzyl or phenethyl, and each $R^2$ is independently H, $CH_3$ or $C_2H_5$, to form a 4-phenyl-4-hydroxypiperidine of the formula

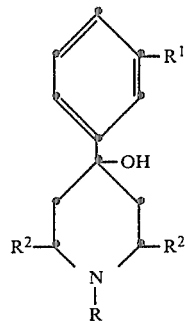

(b) dehydrating said 4-phenyl-4-hydroxypiperidine to yield a 4-phenyl-1,2,5,6,-tetrahydropyridine of the formula

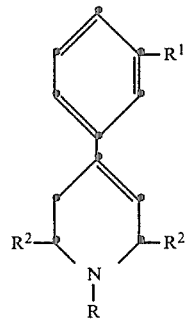

(c) reacting said tetrahydropyridine with n-butyl lithium to form a carbanion and alkylating said carbanion with an α,ω-dihaloalkane of the formula

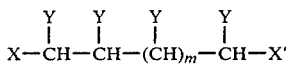

wherein m is 0 or 1, each Y is independently H, $CH_3$ or $C_2H_5$ and X and X' are the same or different members of the group Cl, Br and I, to yield a 4-substituted 4-phenyl-1,4,5,6-tetrahydropyridine of the formula

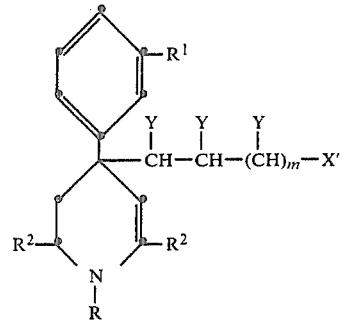

(d) internally cyclizing said 4-phenyl-4-(ω-haloalkyl)-1,4,5,6-tetrahydropyridine to yield a bicyclic derivative of the formula

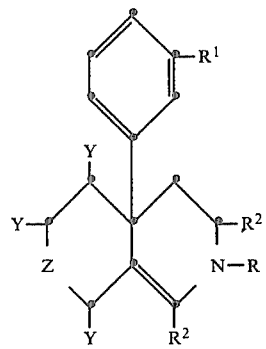

wherein R, $R^1$, $R^2$ and Y have the previously assigned significance and Z is

or a direct bond.

2. A process according to claim 1 in which the internal cyclization of step (d) takes place in dilute acetonitrile solution in the presence of sodium iodide.

3. A process according to claim 1 in which the alkylating agent of step (c) is an α,ω-dihaloalkane of the formula

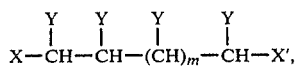

wherein, when X is I, X' is Br or Cl and when X is Br, X' is Cl.

* * * * *